US006433210B1

(12) United States Patent
Lantzsch et al.

(10) Patent No.: US 6,433,210 B1
(45) Date of Patent: Aug. 13, 2002

(54) PROCESS FOR PRODUCING SUBSTITUTED ARYLPYRAZOLES

(75) Inventors: Reinhard Lantzsch, Wuppertal; Thomas Himmler, Odenthal; Albrecht Marhold, Leverkusen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/916,034

(22) Filed: Jul. 26, 2001

Related U.S. Application Data

(62) Division of application No. 09/605,234, filed on Jun. 28, 2000, which is a division of application No. 09/180,223, filed as application No. PCT/EP97/02546 on May 20, 1997, now Pat. No. 6,060,605.

(30) Foreign Application Priority Data

May 30, 1996 (DE) .......................................... 196 21 687

(51) Int. Cl.[7] ...................... C07C 255/56; C07C 49/217

(52) U.S. Cl. ...................................... 558/414; 568/308

(58) Field of Search ........................... 558/414; 568/308

(56) References Cited

U.S. PATENT DOCUMENTS

| 5,182,295 A | 1/1993 | Benoit et al. ................ 514/365 |
| 5,281,571 A | 1/1994 | Woodard et al. ............ 504/225 |
| 5,658,489 A | 8/1997 | Higashii et al. ....... 252/299.01 |

FOREIGN PATENT DOCUMENTS

WO  94/05153  3/1994

OTHER PUBLICATIONS

Recueil Des Travaux Chimiques Des Pays–Bas, vol. 85, No. 2, Feb. 1966, pp. 167–174, W.P. Trompen et al.
Macromolecules, vol. 30, No. 7, Apr. 1997, pp. 1964–1997, m. Moroni et al.
Houben–Weyl: vol. E8b:, Nov. 29, 1994, pp. 472–474.
Journal of the American Chemical Society, vol. 93, Nr. 10, May 19, 1971, pp. 2471–2481, A.G. Hortmann et al.
Synthesis, Nr. 5, May 1996, Stuttgart DE, pp. 589–591, A.G. Mal'Kina et al.
Synthesis, Nr. 8, Aug. 1980, Stuttgart DE, pp. 627–630, S. Takahashi et al.

*Primary Examiner*—Robert W. Ramsuer
*Assistant Examiner*—Ebenezer Sackey
(74) *Attorney, Agent, or Firm*—Joseph C. Gil; Raymond J. Harmuth

(57) ABSTRACT

The invention relates to a process for preparing substituted arylpyrazoles of the general formula (I)

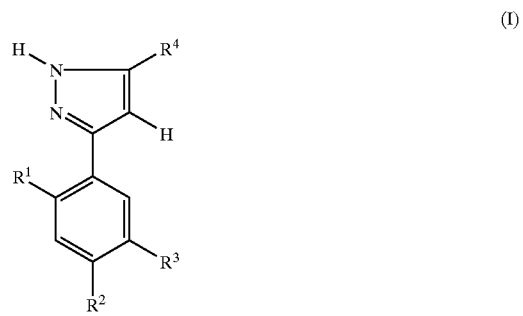

in which
$R^1$, $R^2$, $R^3$ and $R^4$ are each as defined in the description, and to novel intermediates for preparing these arylpyrazoles.

1 Claim, No Drawings

PROCESS FOR PRODUCING SUBSTITUTED ARYLPYRAZOLES

This Application is a divisional of U.S. patent application Ser. No. 09/605,234 filed Jun. 28, 2000, which in turn is a divisional of U.S. patent application Ser. No. 09/180,223 filed May 20, 1997, which is now U.S. Pat. No. 6,060,605 issued May 9, 2000, which in turn is a 35 U.S.C. Section 371 application of PCT/EP97/02546, filed May 20, 1997.

TECHNICAL FIELD OF THE INVENTION

The invention relates to a novel process and novel intermediates for preparing substituted arylpyrazoles which are known as intermediates for herbicides.

BACKGROUND OF THE INVENTION

A number of processes for preparing herbicidally active arylpyrazoles have already been disclosed; however, these processes afford the desired products in not quite satisfactory yields (cf. U.S. Pat. No. 5,281,571).

DETAILED DESCRIPTION OF THE INVENTION

This invention, accordingly, provides a novel process for preparing substituted arylpyrazoles of the general formula (I)

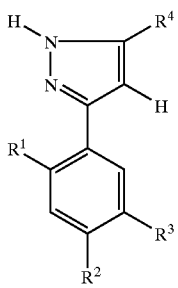

in which
  $R^1$ represents hydrogen or halogen,
  $R^2$ represents cyano or halogen,
  $R^3$ represents halogen, alkyl, halogenoalkyl or alkoxycarbonyl and
  $R^4$ represents option ally substituted alkyl,
  characterized in that in a first step halogenoarenes of the general formula (II)

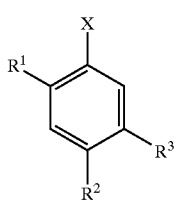

in which
  $R^1$, $R^2$ and $R^3$ are each as defined above and
  X represents halogen
  are reacted with substituted alkines of the general formula (III)

in which
  Z represents 1-hydroxy-isopropyl or trimethylsilyl,
  if appropriate in the presence of one or more reaction auxiliaries and if appropriate in the presence of a diluent, at temperatures between 50° C. and 150° C., the substituted arylalkines formed of the general formula (IV)

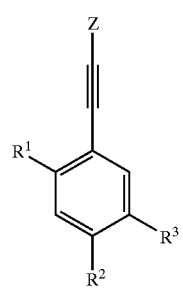

in which
  $R^1$, $R^2$, $R^3$ and Z are each as defined above are reacted
  if appropriate without intermediate isolation
  in a second step with an alkali metal hydroxide or alkaline earth metal hydroxide and/or an alkali metal fluoride or alkaline earth metal fluoride, if appropriate in the presence of a reaction auxiliary and if appropriate in the presence of a diluent, at temperatures between 50° C. and 150° C., the arylalkines formed of the general formula (V)

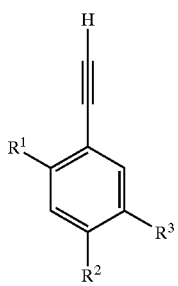

in which
  $R^1$, $R^2$ and $R^3$ are each as defined above
  are reacted in a third step with acylating agents of the general formula (VI)

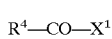

in which
  $R^4$ is as defined above and
  $X^1$ represents halogen or the group —O—CO—O—$R^4$,
  if appropriate in the presence of one or more reaction auxiliaries and if appropriate in the presence of a diluent, at temperatures between 0° C. and 150° C. and the arylalkinones formed of the general formula (VII)

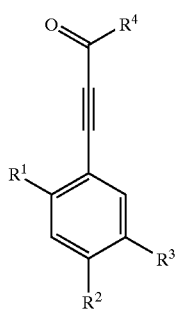

(VII)

in which

R¹, R² R³ and R⁴ are each as defined above are reacted in a fourth step with hydrazine (hydrate), if appropriate in the presence of a diluent, at temperatures between 0° C. and 150° C.

Surprisingly, the substituted arylpyrazoles of the general formula (I) can be obtained in very high yields and in very good quality by the process according to the invention.

The process according to the invention thus represents a useful advance on the prior art.

The process according to the invention preferably relates to the preparation of compounds of the formula (I) in which R¹ represents hydrogen, fluorine or chlorine, R² represents cyano, fluorine or chlorine, R³ represents halogen, $C_1$–$C_6$-alkyl, $C_1$–$C_6$-halogenoalkyl or $C_1$–$C_6$-alkoxy-carbonyl and R⁴ represents optionally fluorine- and/or chlorine-substituted $C_1$–$C_6$-alkyl.

The process according to the invention in particular relates to the preparation of compounds of the formula (I) in which R¹ represents hydrogen, fluorine or chlorine, R² represents cyano or chlorine, R³ represents fluorine, chlorine, methyl, ethyl, trifluoromethyl, methoxycarbonyl or ethoxycarbonyl and R⁴ represents methyl, ethyl, n- or i-propyl, n-, i-, s- or t-butyl, each of which is optionally substituted by fluorine and/or chlorine.

Using, for example, in the first step 4-bromo-3-fluoro-2-methyl-benzonitrile and 2-methyl-3-butin-2-ol as starting materials, reacting in the next stage with sodium hydroxide and then further with dichloroacetyl chloride and finally with hydrazine hydrate, the course of the reaction in the process according to the invention can be outlined by the following formula scheme:

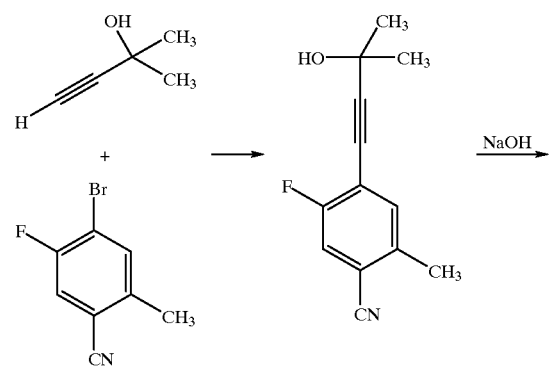

-continued

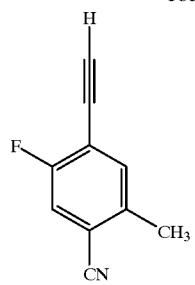

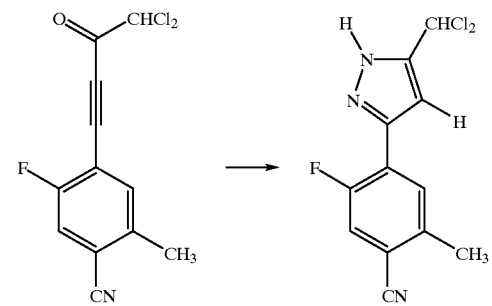

The formula (II) provides a general definition of the halogenoarenes to be used as starting materials in the process according to the invention for preparing compounds of the formula (I). In the formula (II), R¹, R² and R³ each preferably or in particular have those meanings which have already been mentioned above, in connection with the description of the compounds of the formula (I) according to the invention, as being preferred or as being particularly preferred for R¹, R² and R³; X preferably represents chlorine, bromine or iodine, in particular bromine or iodine.

The starting materials of the formula (II) are known and/or can be prepared by known processes (cf. J. Am. Chem. Soc. 81 (1959), 5643; J. Org. Chem. 27 (1962), 1426–1430; loc. cit. 59 (994), 7238–7242; J. Med. Chem. 13 (1970), 713–722).

The compounds of the formula (II) are obtained, for example, when (a) benzene derivatives of the general formula (VIII)

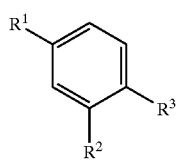

(VIII)

in which

R¹, R² and R³ are each as defined above are reacted with halogenating agents, such as, for example, chlorine, bromine or iodine, if appropriate in the presence of a catalyst, such as, for example, iron, at temperatures between 0° C. and 50° C. (cf. the Preparation Examples), or when
(b) aniline derivatives of the general formula (IX)

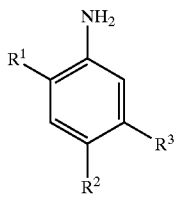

(IX)

in which
R$^1$, R$^2$ and R$^3$ are each as defined above
are reacted with sodium nitrite in the presence of a hydrohalic acid, such as, for example, hydrochloric acid (hydrogen chloride), hydrobromic acid (hydrogen bromide) or hydroiodic acid (hydrogen iodide), if appropriate in the presence of a catalyst, such as, for example, copper(I) chloride, copper(I) bromide or copper(I) iodide, at temperatures between 0° C. and 50° C.

The substituted alkines further to be used as starting materials in the process according to the invention for preparing compounds of the formula (I) are known chemicals for synthesis.

The first step of the process according to the invention is carried out in the presence of one or more reaction auxiliaries.

These include palladium (if appropriate in the presence of a support material, such as, for example, activated carbon), palladium complexes, such as, for example, palladium-bis-(triphenylphosphine) dichloride [bis-(triphenylphosphine)-palladium(II) dichloride] or tetrakis-(triphenylphosphine)-palladium, and also palladium salts, such as, for example, palladium(II) acetate or palladium(II) chloride, if appropriate in the presence of triphenylphosphine and if appropriate in the presence of copper compounds, such as, for example, copper(I) chloride, copper(I) bromide or copper(I) iodide, and also—if appropriate as further reaction auxiliaries—basic organic nitrogen compounds, such as trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2,2,2]-octane (DABCO), 1,5-diazabicyclo[4,3,0]-non-5-ene (DBN), or 1 8 diazabicyclo[5,4,0]-undec-7-ene (DBU).

Suitable diluents for carrying out the process according to the invention are for all steps primarily inert organic solvents. These include in particular aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methyl-pyrrolidone or hexamethylphosphoric triamide; esters such as methyl acetate or ethyl acetate, and also sulphoxides, such as dimethyl sulphoxide.

When carrying out the first step of the process according to the invention, the reaction temperatures can be varied within a relatively wide range. In general, the first step is carried out at temperatures between 50° C. and 150° C., preferably between 80° C. and 120° C.

The first step of the process according to the invention is generally carried out under atmospheric pressure. However, it is also possible to carry out the first step of the process according to the invention under elevated or reduced pressure, in general between 0.1 bar and 10 bar.

For carrying out the first step of the process according to the invention, generally 0.1 to 100 mmol, preferably 1.0 to 50 mmol of a palladium complex, if appropriate 0.1 to 400 mmol, preferably 1.0 to 300 mmol, of triphenylphosphine, if appropriate 1.0 to 400 mmol, preferably 1 to 200 mmol, of a copper compound, and also, if appropriate, 1 to 100 mol, preferably 5 to 50 mol, of a basic organic nitrogen compound are employed per mole of halogenoarene of the formula (II).

In a preferred embodiment of the first step of the process according to the invention, the reaction components and reaction auxiliaries are mixed at room temperature and heated at the required reaction temperature until the reaction has ended. Work-up can be carried out in the customary manner. For example, the reaction mixture is filtered after the reaction has ended and the solvent is carefully distilled off from the filtrate under reduced pressure, the reaction product remaining as residue. However, it is also possible to employ the filtrate directly for the further reaction in the second step.

The second step of the process according to the invention is carried out using an alkali metal hydroxide or alkaline earth metal hydroxide and/or an alkali metal fluoride or alkaline earth metal fluoride. These include, for example, lithium hydroxide, sodium hydroxide, potassium hydroxide, rubidium hydroxide, caesium hydroxide, magnesium hydroxide, calcium hydroxide and barium hydroxide and sodium fluoride, potassium fluoride, caesium fluoride and magnesium fluoride. Preference is given to using sodium hydroxide for carrying out the second step.

For the second step of the process according to the invention, a reaction auxiliary is preferably employed. Suitable reaction auxiliaries are in particular basic organic nitrogen compounds, such as trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2,2,2]-octane (DABCO), 1,5-diazabicyclo[4,3,0]-non-5-ene (DBN), or 1,8 diazabicyclo[5,4,0]-undec-7-ene (DBU).

When carrying out the second step of the process according to the invention, the reaction temperatures can be varied within a relatively wide range. In general, the second step is carried out at temperatures between 0° C. and 150° C., preferably between 20° C. and 120° C.

The second step of the process according to the invention is generally carried out under atmospheric pressure. However, it is also possible to carry out the second step of the process according to the invention under elevated or reduced pressure, in general between 0.1 bar and 10 bar.

For carrying out the second step of the process according to the invention, generally 0.01 to 1.0 mol, preferably 0.1 to 0.5 mol, of alkali metal hydroxide or alkaline earth metal hydroxide and, if appropriate, 1 to 100 mol, preferably 5 to 50 mol, of reaction auxiliary are employed per mole of substituted arylalkine of the formula (IV).

In a preferred embodiment of the second step of the process according to the invention, the filtrate from the first step is admixed at room temperature with an alkali metal hydroxide or alkaline earth metal hydroxide, and the mixture is then heated at the required reaction temperature until the reaction is ended. Work-up can be carried out in a customary manner, for example by distillation under reduced pressure.

The formula (VI) provides a general definition of the acylating agents to be used as reaction components in the third step of the process according to the invention for preparing compounds of the formula (I). In the formula (VI), $R^4$ preferably or in particular has those meanings which have already been mentioned above, in connection with the description of the compounds of the formula (I) according to the invention, as being preferred or as being particularly preferred for $R^4$; $X^1$ preferably represents fluorine, chlorine, bromine or the group O—CO—O—$R^4$, in particular chlorine.

The starting materials of the formula (IV) are known chemicals for synthesis.

The third step of the process according to the invention is carried out in the presence of one or more reaction auxiliaries.

These preferably include copper compounds, such as, for example, copper(I) chloride, copper(I) bromide or copper(I) iodide, and—preferably as further reaction auxiliaries—basic organic nitrogen compounds, such as trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo-[2,2,2]-octane (DABCO), 1,5-diazabicyclo[4,3,0]-non-5-ene (DBN), or 1,8 diazabicyclo[5,4,0]-undec-7-ene (DBU).

When carrying out the third step of the process according to the invention, the reaction temperatures can be varied within a relatively wide range. In general, the third step is carried out at temperatures between 0C and 150° C., preferably between 10° C. and 120° C.

The third step of the process according to the invention is generally carried out under atmospheric pressure. However, it is also possible to carry out the third step of the process according to the invention under elevated or reduced pressure—in general between 0.1 bar and 10 bar.

To carry out the third step of the process according to the invention, in general 0.9 to 2.0 mol, preferably 1.0 to 1.5 mol, of acylating agent of the formula (VI) and, if appropriate, 0.01 to 5.0 mol, preferably 0.1 to 2.5 mol, of reaction auxiliary are employed per mole of arylalkine of the formula (V).

In a preferred embodiment of the third step of the process according to the invention, arylalkine of the formula (V) and reaction auxiliary are mixed Keith the diluent and—preferably at slightly elevated temperature—admixed with the acylating agent. The reaction mixture is then—preferably at elevated temperature and, if appropriate, under elevated pressure—stirred until the reaction has ended. Work-up can be carried out after cooling in a customary manner, for example by washing with dilute hydrochloric acid and then with water, separating off the organic phase and careful distillative removal of the solvent from the organic phase under reduced pressure.

When carrying out the fourth step of the process according to the invention, the reaction temperatures can be varied over a relatively wide range. In general, the fourth step is carried out at temperatures between 0° C. and 150° C., preferably between 20° C. and 120° C.

The fourth step of the process according to the invention is generally carried out under atmospheric pressure. However, it is also possible to carry out the fourth step of the process according to the invention under elevated or reduced pressure—in general between 0.1 bar and 10 bar.

For carrying out the fourth step of the process according to the invention, generally 0.9 to 2.0 mol, preferably 1.0 to 1.5 mol, of hydrazine (hydrate) are employed per mole of arylalkinone of the formula (VII).

In a preferred embodiment of the fourth step of the process according to the invention, the reaction components are mixed at room temperature with a suitable solvent and the reaction mixture is heated until the reaction has ended—preferably on a water separator. Work-up can be carried out in the customary manner, for example by carefully distilling off the solvent under reduced pressure.

The substituted arylalkines of the general formula (IV) obtained in the first step of the process according to the invention, the arylalkines of the general formula (V) obtained in the second step and the arylalkinones of the general formula (VII) obtained in the third step have hitherto not been disclosed in the literature. The compounds of the general formulae (IV), (V) and (VII) therefore also form, as novel substances, part of the subject-matter of the present application.

The substituted arylpyrazoles of the formula (I) preparable by the process according to the invention can be employed as intermediates for preparing herbicidally active compounds (cf. U.S. Pat. No. 5281571).

PREPARATION EXAMPLES
Carrying Out the First Step

Example (IV-1)

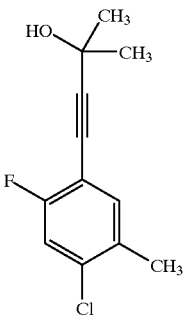

A mixture of 4.47 g (20 mmol) of 3-bromo-6-chloro-4-fluoro-toluene. 2.02 g (24 mmol) of 2-methyl-3-butin-2-ol, 14 mg (0.02 mmol) of palladium-bis-(triphenylphosphine) dichloride, 42 mg (0.16 mmol) of triphenyiphosphine. 15 mg (0.08 mmol) of copper(I) iodide and 20 ml of triethylamine is heated at reflux under an atmosphere of nitrogen for 4 hours. The mixture is then filtered and the filtercake is washed with some ml of triethylamine, and the volatile components of the filtrate are carefully distilled off under water pump vacuum.

This gives 4.4 g (95% pure, i.e. 92% of theory) of 1-(4-chloro-2-fluoro-5-methyl-phenyl)-3-methyl-1-butin-3-ol as a yellow oil.

$^1$H NMR (400 MHz, CDCl$_3$, d, ppm): 1.63 (s, 6H, C(CH$_3$)$_2$), 2.28 (s, 3H, Ar—CH$_3$), 2.5 (s, 1H, OH), 7.08 (d, J=9Hz, 1H, Ar—H), 7.25 (d, J=7Hz, 1H, Ar—H).

Example (IV-2)

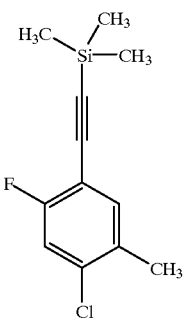

Under an atmosphere of nitrogen, a mixture of 11.2 g (50 mmol) of 3-bromo-6-chloro-4-fluoro-toluene, 5.9 g (60 mmol) of trimethylsilylacetylene, 175 mg (0.25 mmol) of palladium-bis-(triphenylphosphine)dichloride, 525 mg (2 mmol) of triphenylphosphine, 190 mg (1 mmol) of copper(I) iodide and 20 ml of triethylamine is heated at reflux for 11 hours. The mixture is then filtered, the filtercake is washed with some ml of triethylamine and the filtrate is concentrated under water pump vacuum. The residue is taken up in methylene chloride, washed with water, dried with sodium sulphate and filtered. The volatile components of the filtrate are carefully distilled off under water pump vacuum.

This gives 10.6 g (95% pure, i.e. 83% of theory) of trimethyl-(4-chloro-2-fluoro-5-methyl-phenyl-ethinyl)-silane as an orange oil.

Carrying Out the Second Step

Example (V-1)

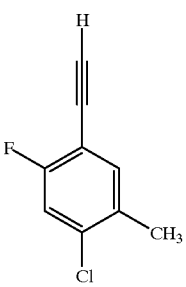

By the method of Example (IV-1), 100 mmol of 3-bromo-6-chloro-4-fluoro-toluene are reacted with 2-methyl-3-butin-2-ol to give 1-(4-chloro-2-fluoro-5-methyl-phenyl)-3-methyl-1-butin-3-ol, except that the mixture is only filtered after the reaction and not concentrated. The filtrate is then admixed with 1.5 g of sodium hydroxide (powder) and the mixture is heated to the boil in a distillation apparatus (with Vigreux column). Distillate is continuously removed, until the boiling point of triethylamine (89° C.) is reached. The mixture is then allowed to cool, filtered and flashed with some ml of triethylamine. The filtrate is subsequently subjected to fractional distillation.

This gives 12.8 g (98% pure, i.e. 74% of theory) of (4-chloro-2-fluoro-5-methyl-phenyl)-ethine of boiling point 81° C. to 82° C. at 10 mbar which solidifies on cooling.

Melting point: 60° C.

$^1$H NMR (400 MHz, CDCl$_3$, d, ppm): 2.3 (s, 3H, Ar—CH$_3$), 3.3 (s, 1H, C—CH), 7.1 (d, J=9Hz, 1H, Ar—H), 7.33 (d, J=7Hz, 1H, Ar—H).

Carrying Out the Third Step

Example VII-1)

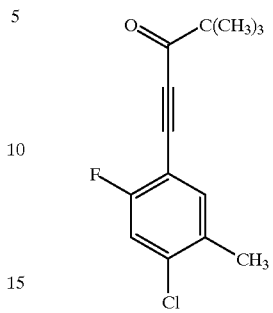

Under argon, a mixture of 2 g (20 mmol) of triethylamine, 0.3 g (2 mmol) of copper(I) bromide, 3.4 g (20 mmol) of (4-chloro-2-fluoro-5-methyl-phenyl)-ethine and 15 ml of toluene is stirred at room temperature (about 20° C.) for approximately 30 minutes. The mixture is heated to 50° C., 2.4 g (20 mmol) of pivaloyl chloride are added dropwise and the mixture is then stirred at about 90° C. for approximately 12 hours. After cooling, the mixture is washed with 2N hydrochloric acid and with water and then concentrated—initially under water pump vacuum, then under oil pump vacuum.

This gives 4.4 g (92.3% pure, i.e. 80% of theory) of 4,4-dimethyl-1-(4-chloro-2-fluoro-5-methyl-phenyl)-1-pentin-3-one as an oil with a red tinge.

Example (VII-1)

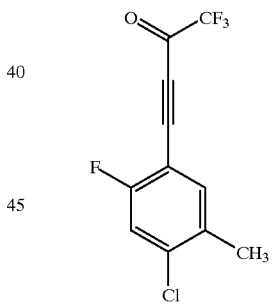

In an autoclave and under argon, a mixture of 2 g (20 mmol) of triethylamine, 0.3 g (2 mmol) of copper(I) bromide, 3.4 g (20 mmol) of (4-chloro-2-fluoro-5-methyl-phenyl)-ethine and 15 ml of toluene are stirred at room temperature (about 20° C.) for approximately 30 minutes. 3.3 g (25 mmol) of trifluoroacetyl chloride are then introduced, the autoclave is closed and the mixture is heated at 90° C. for approximately 12 hours. The autoclave is allowed to cool and vented and the mixture is washed with 2N hydrochloric acid and with water and then concentrated—initially under water pump vacuum, then under oil pump vacuum.

This gives 4.7 g (88% of theory) of 4,4,4-trifluoro-1-(4-chloro-2-fluoro-5-methyl-phenyl)-1-butin-3-one as a slowly solidifying oil with a red tinge. Melting point: 33° C.

Carrying Out the Fourth Step

Example (I-1)

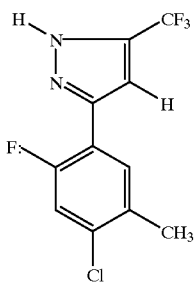

A mixture of 930 mg (3.5 mmol) of 4,4,4-trifluoro-1-(4-chloro-2-fluoro-5-methyl-phenyl)-1-butin-3-one, 175 mg (3.5 mmol) of hydrazine hydrate and 5 ml of toluene is heated to the boil on a water separator for approximately 3 hours. The solvent is then carefully distilled off under reduced pressure.

This gives 900 mg (92% of theory) of 3-(4-chloro-2-fluoro-5-methyl-phenyl)-5-trifluoromethyl-1H-pyrazole of melting point 159° C.

Example (I-2)

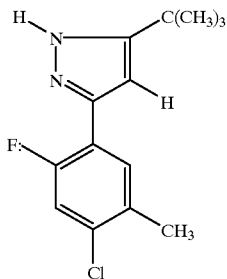

A mixture of 525 mg (1 mmol) of 4,4-dimethyl-1-(4-chloro-2-fluoro-5-methyl-phenyl)-1-pentin-3-one, 52 mg (1.1 mmol) of hydrazine hydrate and 10 ml of toluene is heated to the boil on a water separator for approximately 6 hours. The solvent is then carefully distilled off under reduced pressure.

This gives 2.6 g (95% of theory) of 3-(4-chloro-2-fluoro-5-methyl-phenyl)-5-t-butyl-1H-1-pyrazole of melting point 138° C.

Starting materials of the formula (II)

Example (II-1)

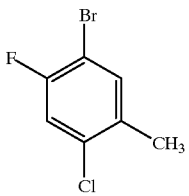

At 25° C. to 30° C., 180 g (1.125 mol) of bromine are added dropwise to a mixture of 144 g (1.0 mol) of 2-chloro-4-fluoro-toluene and 1 g of iron (powder), resulting in a strong evolution of gas. After the addition, the mixture is stirred at about 30° C. for approximately 2 hours. 100 ml of water are then added, and the mixture is decolourized by addition of sodium bisulfite. The organic phase is then separated off and distilled under reduced pressure.

This gives 188 g (82% of theory) of 3-bromo-2-chloro-4-fluoro-toluene of boiling point 67° C. to 68° C. at 10 mbar.

Refractive index: =1.5535.

The compound 3-bromo-2-chloro-4-fluoro-toluene preparable by Example (II-1) has hitherto not been disclosed in the literature; as a novel substance, it also forms part of the subject-matter of the present application.

What is claimed is:

1. An arylalkinone of the general formula (VII)

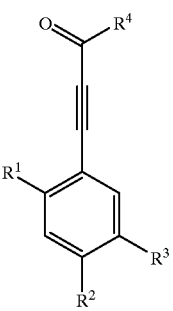

wherein $R^1$ represents hydrogen or halogen, $R^2$ represents cyano or halogen, $R^3$ represents halogen, alkyl, halogenoalkyl or alkoxycarbonyl, and $R^4$ represents unsubstituted or substituted alkyl.

* * * * *